United States Patent

Asai et al.

[11] Patent Number: 5,804,040
[45] Date of Patent: Sep. 8, 1998

[54] PURIFICATION PROCESS FOR SILANE COMPOUND

[75] Inventors: Yousuke Asai, Kobe; Nobuo Ogawa, Akashi, both of Japan

[73] Assignee: Kaneka Corporation, Osaka, Japan

[21] Appl. No.: 709,534

[22] Filed: Sep. 6, 1996

[30] Foreign Application Priority Data

Sep. 8, 1995 [JP] Japan ................................. 7-255824
Sep. 8, 1995 [JP] Japan ................................. 7-255825

[51] Int. Cl.$^6$ .............................. B01D 3/34; B01D 3/36; C07F 7/20
[52] U.S. Cl. ................................. 203/57; 203/60; 203/75; 203/78; 203/82; 203/84; 556/466; 556/482
[58] Field of Search ................................. 203/60, 57, 65, 203/74, 81, 75, 82, 78, 84, DIG. 23; 556/466, 470, 482

[56] References Cited

U.S. PATENT DOCUMENTS

| | | | |
|---|---|---|---|
| 4,204,915 | 5/1980 | Kurata et al. | 203/DIG. 23 |
| 4,471,133 | 9/1984 | Hallgren | 556/471 |
| 5,084,589 | 1/1992 | Legrow | 556/470 |
| 5,504,235 | 4/1996 | Hirose et al. | 556/467 |

FOREIGN PATENT DOCUMENTS

| | | |
|---|---|---|
| 41489 | 2/1995 | Japan . |
| 8-59837 | 3/1996 | Japan . |
| 319294 | 12/1996 | Japan . |

Primary Examiner—Virginia Manoharan
Attorney, Agent, or Firm—Foley & Lardner

[57] ABSTRACT

There is provided a purification process for dimethoxymethylsilane in which a mixture containing dimethoxymethylsilane and methanol is subjected to a first distillation step in which the mixture is distilled in the presence of methyl formate or methoxytrimethylsilane so that a distillate fraction containing methanol and methyl formate or methoxytrimethylsilane is distilled off and a balance fraction containing dimethoxymethylsilane and methanol is discharged, the amount of methanol in the balance fraction being substantially reduced relative to that of the mixture.

7 Claims, 4 Drawing Sheets

MTMS - MeOH VAPOR - LIQUID EQUILIBRIUM

PURIFICATION PROCESS FOR SILANE COMPOUND

BACKGROUND OF THE INVENTION

1. Field of the Invention

The present invention relates to a purification process for dimethoxymethylsilane which is one of the important intermediates in the silicone industry. Particularly, the present invention relates to a purification process resulting in dimethoxymethylsilane of a high purity in a high yield.

2. Description of the Related Art

Dimethoxymethylsilane is often produced with methanol as one of the starting materials. Also, methanol is produced when dimethoxymethylsilane decomposes. Therefore, methanol and dimethoxymethylsilane often co-exist. Since methanol is highly reactive with regards to the SiH group of dimethoxymethylsilane, the presence of methanol in dimethoxymethylsilane reduces the storage stability of dimethoxymethylsilane. Further to this matter, methanol adversely affects the reactivity of dimethoxymethylsilane as a reaction intermediate.

Therefore, it is important to remove methanol from a liquid mixture of dimethoxymethylsilane and methanol. Since the boiling point of dimethoxymethylsilane is different from that of methanol by only about three or four degrees centigrade, it is very difficult to separate methanol from dimethoxymethylsilane by a conventional distillation process.

The present inventors have measured vapor-liquid equilibriums in a system of dimethoxymethylsilane and methanol, and found that the system forms an azeotropic mixture of which the molar ratio of dimethoxymethylsilane to methanol is about 6:4 (boiling point: about 50° C.) at a pressure of 1 atm.

It has also been confirmed by the inventors that the separation of dimethoxymethylsilane from methanol is very difficult because, as can be seen from FIG. 1, a graph showing the vapor-liquid equilibrium curve of a binary system of methanol and dimethoxymethylsilane at a pressure of 1 atm, the vapor liquid equilibrium curve lies so close to the straight diagonal line on the x-y diagram, especially at higher concentrations of dimethoxymethylsilane.

Thus, dimethoxymethylsilane cannot easily be separated from methanol so that dimethoxymethylsilane containing a slightly reduced concentration of methanol is distilled off from the column even if the liquid mixture of dimethoxymethylsilane and methanol were to be subjected to a conventional distillation process.

SUMMARY OF THE INVENTION

It is, therefore, an object of the present invention to provide a process in which a mixture of dimethoxymethylsilane and methanol is separated so that dimethoxymethylsilane in which the methanol concentration is considerably reduced is obtained.

The present inventors have studied various compounds which change the vapor-liquid equilibrium between methanol and dimethoxymethylsilane, and found that methyl formate acts as an extracting agent (or a solvent) during the distillation operation of a binary system of dimethoxymethylsilane and methanol. In other words, the system can be treated using an extractive distillation operation in which methyl formate is used as the extracting agent. Since the presence of methyl formate in the system of methanol and dimethoxymethylsilane so changes the vapor-liquid equilibrium to the extent that a vapor-liquid equilibrium curve deviates greatly from the diagonal line. Therefore, dimethoxymethylsilane can easily be substantially separated from methanol using a distillation operation with the aid of methyl formate. Furthermore, the equilibrium may exhibit no azeotropic phenomenon when methyl formate present is in excess of a certain amount. This means the that even though there is a possibility of dimethoxymethylsilane and methanol forming an azeotropic mixture, the possibility is eliminated by the presence of methyl formate in that certain amount.

In addition, the present inventors have also found that a binary system of methoxytrimethylsilane and methanol forms an azeotropic mixture of which the molar ratio of methoxytrimethylsilane to methanol is about 6:4 as at a pressure of 1 atm (boiling point: about 50° C.). Thus, when methoxytrimethylsilane is present during the distillation operation of a mixture of dimethoxymethylsilane and methanol, it is possible to distill off the methanol with methoxytrimethylsilane as an azeotropic mixture and to recover dimethoxymethylsilane having a boiling point of 61° C. as a bottom product. In this distillation operation, the formation of an azeotropic mixture of methanol and dimethoxymethylsilane should be avoided. For this purpose, methoxytrimethylsilane is added to the distillation system in order that all the methanol forms the azeotropic mixture with methoxytrimethylsilane.

Thus, the present invention provides a purification process for dimethoxymethylsilane characterized in that a mixture comprising dimethoxymethylsilane and methanol is subjected to a distillation step in which the mixture is distilled in the presence of methyl formate and/or methoxytrimethylsilane so that a distillate fraction comprising methanol and said methyl formate and/or methoxytrimethylsilane is distilled off and a balance fraction comprising dimethoxymethylsilane and methanol is discharged, the amount of methanol remaining in the balance fraction being substantially reduced relative to that of the mixture.

In the present invention, the balance fraction describes the fraction which is obtained by subtracting the distillate fraction from the mixture (i.e. the mixture minus the distillate fraction). However, the balance fraction is not always said fraction but may be a portion of said fraction. Considering a continuous distillation operation in a steady state condition, the distillate fraction plus the balance fraction gives the mixture. However, in a batchwise distillation, after the distillate fraction has been distilled off, there is a possibility that a series of distillates are subsequently distilled off with or without some remainder in a still of the column. Thus, the term balance fraction is also intended to mean at least one of such subsequent distillates and any remainder in the still.

More concretely, the present invention provides:

a purification process for dimethoxymethylsilane in which a mixture comprising dimethoxymethylsilane and methanol is subjected to an extractive distillation step using methyl formate as an extractive agent (or a solvent) and thus a distillate fraction comprising methanol together with methyl formate is distilled off and a balance fraction comprising dimethoxymethylsilane and methyl formate is discharged, the amount of methanol remaining in the balance fraction being substantially reduced relative to that of the original mixture;

a purification process of dimethoxymethylsilane in which a mixture comprising dimethoxymethylsilane and methanol is subjected to an azeotropic distillation step using methoxytrimethylsilane as an azeotropic agent (or an entrainer) and thus a distillate fraction comprising methanol and methoxytrimethylsilane is distilled off and a balance fraction comprising dimethoxymethylsilane is discharged, the amount of methanol remaining in the balance fraction being substantially reduced in relative to that of the original mixture;

a combination of the two processes outlined above, namely a purification process for dimethoxymethylsilane in which a mixture comprising dimethoxymethylsilane and methanol is distilled in the presence of both methyl formate and methoxytrimethylsilane so as to separate methanol together with methyl formate and methoxytrimethylsilane as a distillate fraction from a balance fraction comprising dimethoxymethylsilane and methyl formate where the amount of methanol remaining in the balance fraction is substantially reduced relative to that of the original mixture.

As seen from the vapor-liquid equilibrium curve shown in FIG. 1, the process of the present invention is effective when the concentration of dimethoxymethylsilane is not less than about 60% by mole based on the mixture of dimethoxymethylsilane and methanol. When the concentration of dimethoxymethylsilane is less than 60% by molar, a portion of dimethoxymethylsilane purified according to the present process may be added to the mixture so as to increase the concentration to not less than 60% by mole.

In a preferred embodiment of the present invention, the balance fraction contains methanol of which the amount is substantially less than 20%, more preferably less than 10%, most preferably less than 1% of the amount of methanol contained in the mixture. In the most preferable embodiment, the amount of methanol contained in the balance fraction is substantially almost zero.

In one embodiment of the present invention, the mixture which is to be subjected to the step consists substantially of dimethoxymethylsilane and methanol. It is of course possible for the mixture to contain other compounds such as methoxymethylsilane and a dimer of dimethoxymethylsilane as long as they do not adversely affect the present process. Those other compounds are contained in the distillate and/or the balance fractions depending on their properties, especially their vapor-liquid equilibrium properties in relation to any other compounds present.

DETAILED DESCRIPTION OF THE INVENTION

Firstly, the purification process using methyl formate will be explained in detail.

Figure 1:
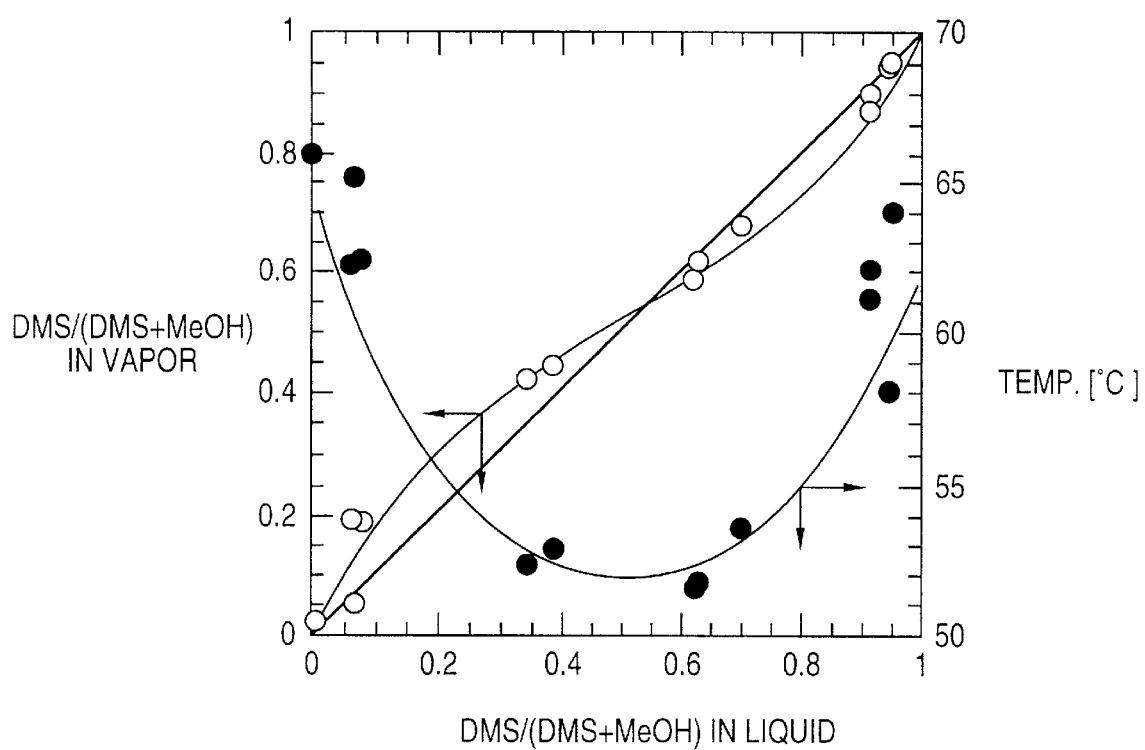
FIG. 1 is a graph which shows a vapor-liquid equilibrium and a boiling point curve based on a molar ratios of a binary system of dimethoxymethylsilane (DMS) and methanol (MeOH) at a pressure of 1 atm.
Figure 2:
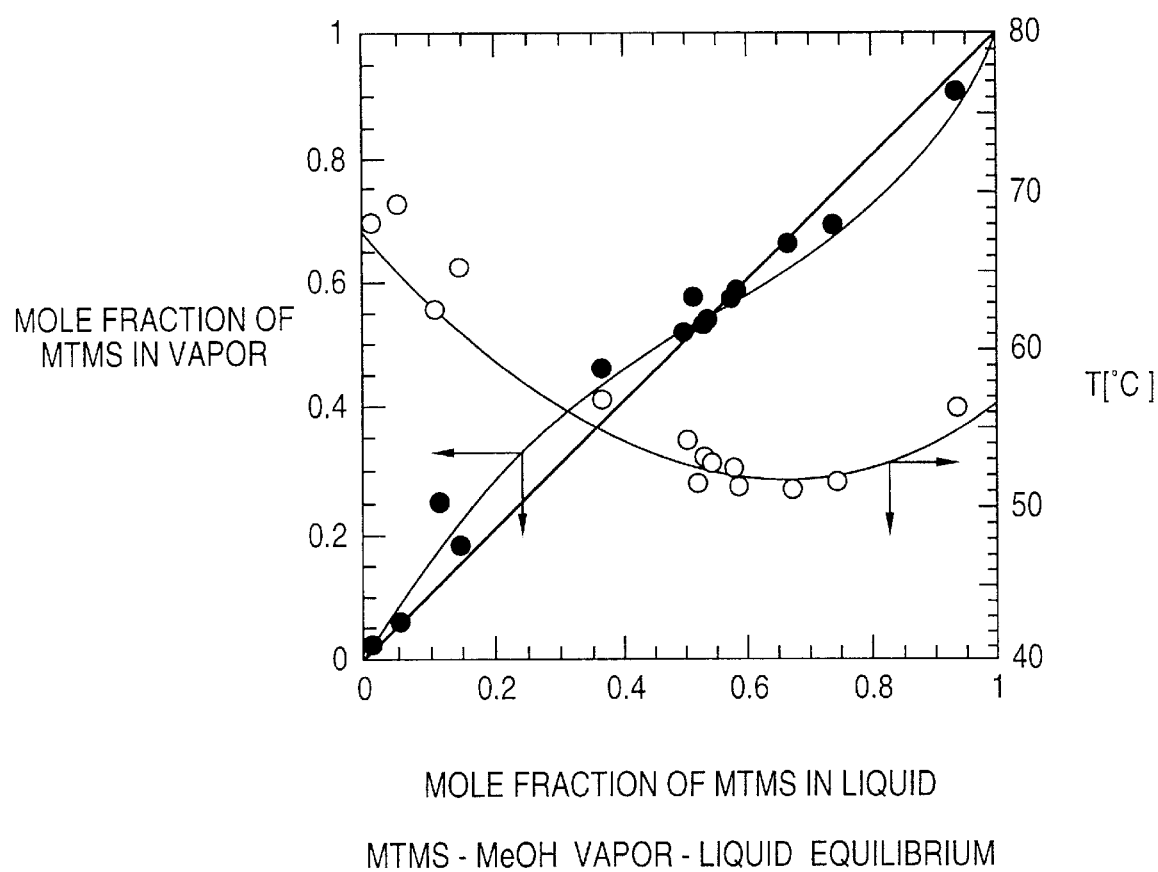
FIG. 2 is a graph which shows a vapor-liquid equilibrium and a boiling point curve based on a molar ratio of a binary system of methoxytrimethylsilane (MTMS) and methanol (MeOH) at a pressure of 1 atm.
Figure 3:
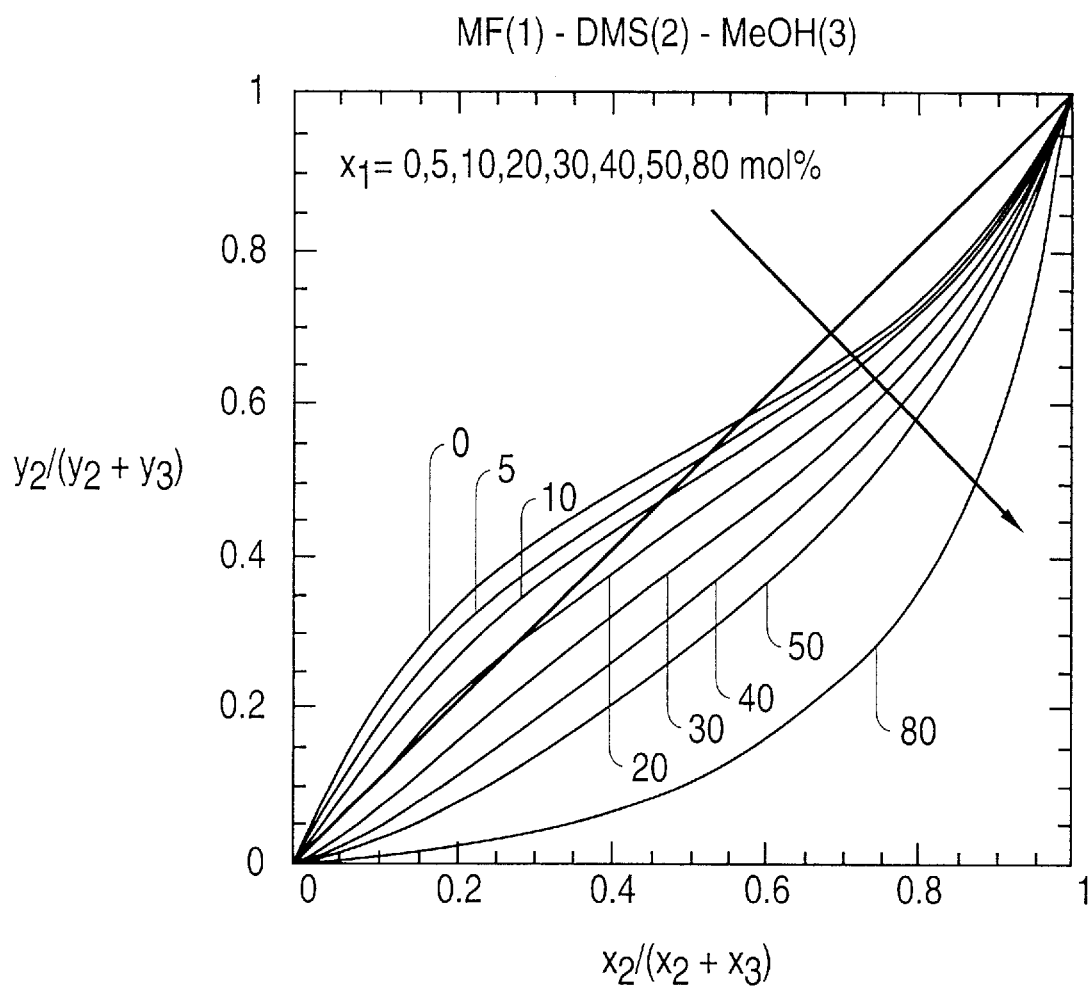
FIG. 3 is a graph which shows the effects of the presence of methyl formate on vapor-liquid equilibrium curves based on mole ratios between dimethoxymethylsilane ($x_2$ or $y_2$) and methanol ($x_3$ or $y_3$) in a trinary system of methyl formate (MF(1)), dimethoxymethylsilane (DMS(2)) and methanol (MeOH(3)) at a pressure of 1 atm.

Referring to FIG. 3, x and y are molar fractions in a liquid and vapor phase respectively of the trinary system containing methyl formate, dimethoxymethylsilane and methanol. The subscripts 1, 2 and 3 indicate methyl formate, dimethoxymethylsilane and methanol, respectively. The graph of FIG. 3 includes eight curves. These indicate the methyl formate ratio which is increased from 0% stepwise through 5, 10, 20, 30, 40 and 50% to 80% by mole along the direction of the arrow shown in the graph. As can be seen from FIG. 3, when an amount of methyl formate present in the trinary system is increased, the vapor-liquid equilibrium which originally exhibits the azeotropic phenomenon is so shifted that the dimethoxymethylsilane molar fraction in the liquid phase at a given dimethoxymethylsilane molar fraction in the vapor phase tends to increase and dimethoxymethylsilane and methanol do not exhibit azeotropic behavior above a critical methyl formate fraction. Particularly, it has been found that when methyl formate is contained in the liquid phase in an amount of not less than 20% by mole, no azeotropic mixture is formed.

Therefore, when methyl formate is present during the distillation operation of a binary system of dimethoxymethylsilane and methanol, it is possible to separate dimethoxymethylsilane from methanol easily since methyl formate so changes the vapor-liquid equilibriums to the extent that the vapor-liquid equilibrium curve deviates greatly from the diagonal line due to the presence of the extracting agent. In order that the formation of an azeotropic mixture of dimethoxymethylsilane and methanol is avoided, the amount of methyl formate in the liquid phase throughout the distillation column is preferably not less than 20% by mole, more preferably not less than 30% by mole and most preferably not less than 40% by mole.

Since the pressure of the trinary system of methyl formate, dimethoxymethylsilane and methanol has almost no effect on the vapor-liquid equilibrium of the system over an industrially applicable pressure range, the operation pressure of the present invention is not specifically limited provided that the pressure had any adverse effect on the present process. For example, the operation pressure in a range between 1 atm and 5 atm may be employed in the present invention.

The present inventors have further measured vapor-liquid equilibriums of a binary system of methyl formate and dimethoxymethylsilane and found based on their results thereof that the binary system forms no azeotropic mixture and separation of methyl formate from dimethoxymethylsilane is relatively straightforward. This means that methyl formate added as the extracting agent can be separated from dimethoxymethylsilane through a conventional distillation process, and methyl formate and dimethoxymethylsilane are recovered at high purities, the former to be re-used as an extracting agent and the latter as the final product of the purification process. Thus, the balance fraction comprising methyl formate and dimethoxymethylsilane from the extractive distillation (usually, discharged from the distillation as a bottom fraction during a continuous mode) may be subjected to a conventional distillation and it is easily separated into methyl formate and dimethoxymethylsilane.

Since methyl formate has a boiling point which is about 30° C. below that of methanol and these two compounds form no azeotropic mixture, they can easily be separated from each other by a conventional distillation operation. This means that the distillate fraction comprising methyl formate and methanol is easily separated into methyl formate to be re-used as an extracting agent and methanol which can be recycled to a reaction step for the production of dimethoxymethylsilane, whereby each has a high purity.

The present purification process using the extractive distillation is explained with reference to FIG. 4, which shows schematically one example of the preferred embodiments. The process is carried out using two distillation columns 1 and 2. Distillation column 1 works as an extractive distillation column which separates methanol from dimethoxymethylsilane, and distillation column 2 works as a conventional distillation column which separates methyl formate as the extractive agent from dimethoxymethylsilane as the product.

A mixture of methanol and dimethoxymethylsilane is supplied to the distillation column 1 as a feed 3. The mixture 3 is subjected to the extractive distillation step in column 1 so that methanol is distilled off together with methyl formate as a top effluent 4 (i.e. the distillate fraction) and dimethoxymethylsilane is discharged together with methyl formate as a bottom effluent 5 (i.e. the balance fraction).

The bottom effluent 5 is supplied to the distillation column 2 which distills off methyl formate as an effluent 6 at the top and discharges dimethoxymethylsilane as an effluent 7 from at the bottom. The top effluent 6 may be recycled to the distillation column 1 so as to re-use it as the extracting agent. Since methyl formate has a normal boiling point of 31° C., methyl formate to be recycled is supplied to a plate (or tray) which is below a plate to which the feed mixture 3 is supplied so as to keep the presence of methyl formate throughout the column 1 preferably at a relatively higher concentration (i.e. enough high so as not to allow the formation of an azeotropic mixture of dimethoxymethylsilane and methanol).

When the distillate fraction 4 contains a relatively large amount of methyl formate (for example 30% by mole), it is supplied to another separate column which separates methyl formate from methanol. The separated methyl formate may preferably be re-used in column 1.

Figure 4:
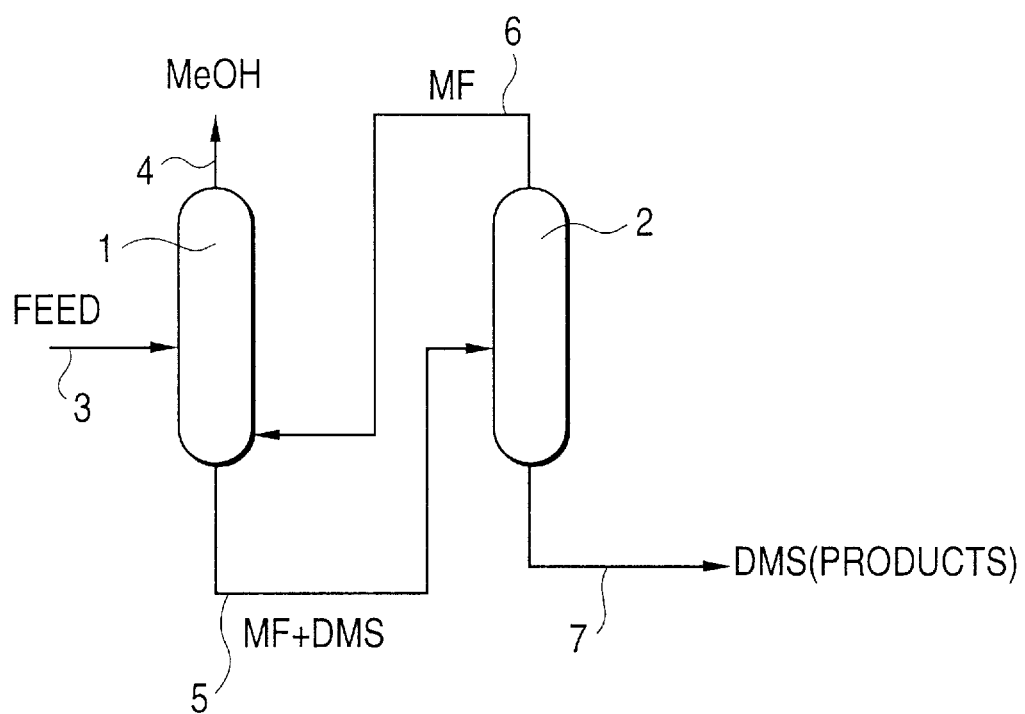
FIG. 4 shows schematically a process flow sheet for the present invention.

Upon starting up the process shown in FIG. 4, methyl formate is supplied to the bottom of column 1. When the columns have reached a steady state condition, the supply of methyl formate to the bottom is stopped and recovered methyl formate is recycled from column 2 to column 1 so that fresh methyl formate no longer needs to be supplied.

The above described operation is a continuous purification operation, but it is of course possible to operate the purification batchwise.

In a production process of dimethoxymethylsilane using a siloxane or a polysiloxane as the starting material as described in Japanese Patent Kokai Publication No. 8-59837, methyl formate is formed as a by-product. When the reaction mixture formed in such a production process is subjected to the present process, methyl formate need not necessarily be added in the extractive distillation operation depending on the amount of methyl formate contained in the reaction mixture.

Next, the present process using methoxytrimethylsilane as an azeotropic agent will be explained in detail.

This distillation operation in the presence of methoxytrimethylsilane can be also carried out either continuously or batchwise. The following description relates to the batchwise mode. Those skilled in the art would easily conceive of a continuous mode having read the following description.

In this present process, methoxytrimethylsilane is used as an azeotropic agent which is added to a mixture of methanol and dimethoxymethylsilane and the resulting mixture is distilled batchwise. It should be noted that the azeotropic agent may be added directly to the distillation column.

An azeotropic mixture of methoxytrimethylsilane and methanol is distilled off first as the distillate fraction since the mixture exhibits the lowest boiling point, and then after substantially all the methanol has been distilled off, dimethoxymethylsilane is distilled off as the balance fraction when the top of the column reaches a temperature of about 61° C. Instead of being distilled off, we may consider dimethoxymethylsilane remaining in the column still as the balance fraction. In the continuous mode, dimethoxymethylsilane of which the amount of methanol is reduced may be discharged from the bottom of the column as the balance fraction while the azeotropic mixture is distilled off as the distillate fraction.

Since the azeotropic mixture of methoxytrimethylsilane and methanol is not easily separated from dimethoxymethylsilane, the reflux ratio is considerably large, for example 100, when the azeotropic mixture is distilled off while dimethoxymethylsilane is left in the column.

The amount of methoxytrimethylsilane in the mixture of dimethoxymethylsilane and methanol is at least the amount which is required to form an azeotropic mixture with all the methanol contained in the mixture. The distillate fraction comprising methanol and methoxytrimethylsilane may be recycled to a reaction process for the production of dimethoxymethylsilane. Alternatively, the distillate fraction may be subjected to a conventional distillation operation so as to separate methoxytrimethylsilane from methanol; the former can then be recycled to the azeotropic distillation step while the latter can be used in the reaction process mentioned above.

Since the pressure of the trinary system of methanol, dimethoxymethylsilane and methoxytrimethylsilane has almost no effect on the vapor-liquid equilibrium of the system over an industrially applicable pressure range, the operation pressure of the present invention is not specifically limited provided that the pressure has no adverse effect on the present process. For example, the operation pressure in a range between 1 atm and 10 atm may be employed in the present invention.

In the production process of dimethoxymethylsilane using a siloxane or a polysiloxane as the starting material as described in Japanese Patent Kokai Publication No. 8-59837, methoxytrimethylsilane is formed as a by-product in an amount of about 2 to 10% by weight. When the effluent from the process as such is subjected to the present process, methoxytrimethylsilane need not necessarily be added as the azeotropic agent depending on the amount of methoxytrimethylsilane contained in the reaction mixture.

EXAMPLES

Example 1

A packed distillation column for the batch mode was used which had an inner diameter of 18 mm and a packing height of 480 mm. The packing material was a glass bead having a diameter of 5 mm, and the column had five theoretical plates. 137.6 grams of a mixture containing dimethoxymethylsilane (54.6% by weight), methanol (1.8% by weight), methoxytrimethylsilane (2.4% by weight) and other compounds (41.2% by weight) were charged into the still in the column, which was then heated.

After the column was operated at a total reflux condition to reach a steady state and when the temperature of the top of the column reached between 50° and 58° C., a distillate fraction of methanol and methoxytrimethylsilane as an azeotropic mixture and excessive methoxytrimethylsilane were distilled off.

Then, with a top temperature of the column between 58° and 62° C., 60.1 g of a distilled fraction was recovered. The recovered fraction was analyzed using gas chromatography and it was found that it contained 97.1% by weight of dimethoxymethylsilane, 0.1% by weight of methanol and 2.4% by weight of the other compounds.

Example 2

A packed distillation column for the batch mode was used which had an inner diameter of 150 mm and a packing height of 6 m. The packing material was a regular packing made of stainless steal (specific surface area: 500 $m^2/m^3$), and the column had twenty theoretical plates. 82.3 kilograms of a mixture which contained dimethoxymethylsilane (49.8% by weight), methanol (2.3% by weight), methoxytrimethylsilane (2.1% by weight) and other compounds (45.8% by weight) was charged into a still of the column), and then the column was heated.

After a total reflux operation for about two hours, some distillates were distilled off in series. With a top temperature of the column between 40° and 55° C., a distillate fraction of methanol and methoxytrimethylsilane as the azeotropic mixture and excessive methoxytrimethylsilane was distilled off. Then, with a top temperature of the column between 55° and 61.5° C., 38.8 kg of a distilled fraction were recovered. The recovered fraction was analyzed using gas chromatography and it was found that it contained 96.3% by weight of dimethoxymethylsilane, 0.9% by weight of methanol and 1.2% by weight of the other compounds.

What is claimed is:

1. A method of purification of dimethoxymethylsilane from a starting mixture comprising methanol and dimethoxymethylsilane, said method comprising:

distilling the starting mixture in the presence of a sufficient amount of methyl formate to prevent formation of an azeotropic mixture between said dimethoxymethylsilane and said methanol, in order to produce (A) a distillate fraction comprising methanol and methyl formate and (B) a balance fraction comprising dimethoxymethylsilane, methyl formate and methanol, whereby said balance fraction (B) is substantially reduced in methanol relative to the starting mixture.

2. A method of purification of dimethoxymethylsilane according to claim 1, wherein said distillate fraction (A) comprising methanol and methyl formate is further distilled to separate methyl formate.

3. A method of purification of dimethoxymethylsilane according to claim 2, further comprising recovering said separated methyl formate.

4. A method of purification of dimethoxymethylsilane as claimed in claim 3, further comprising recycling of said recovered methyl formate to separate dimethoxymethylsilane from said starting mixture.

5. A method of purification of dimethoxymethylsilane as claimed in claim 1, wherein said methyl formate comprises at least 20% by mole of a liquid phase in a distillation column.

6. A method of purification of dimethoxymethylsilane from a starting mixture comprising methanol and dimethoxymethylsilane, said method comprising:

distilling the starting mixture in the presence of methoxytrimethylsilane to form an azeotropic mixture with the methanol contained in said starting mixture, in order to produce (A) a distillate fraction comprising methanol and methoxytrimethylsilane and (B) a balance fraction comprising dimethoxymethylsilane and methanol, whereby said balance traction (B) is substantially reduced in methanol relative to the starting mixture.

7. A method of purification of dimethoxymethylsilane according to claim 6, further comprising distilling said distillate fraction to separate methoxytrimethylsilane.

* * * * *